US007834173B2

(12) United States Patent
Pietrangelo et al.

(10) Patent No.: US 7,834,173 B2
(45) Date of Patent: Nov. 16, 2010

(54) ESTERS OF HYALURONIC ACID WITH RHEIN, PROCESS FOR THEIR PREPARATION AND COMPOSITIONS COMPRISING THE SAME

(75) Inventors: Antonello Pietrangelo, Modena (IT); Valter Travagli, Siena (IT)

(73) Assignee: Laboratoire Medidom S.A., Geneva (CH)

( * ) Notice: Subject to any disclaimer, the term of this patent is extended or adjusted under 35 U.S.C. 154(b) by 444 days.

(21) Appl. No.: 10/590,625

(22) PCT Filed: Feb. 25, 2005

(86) PCT No.: PCT/IB2005/000506

§ 371 (c)(1), (2), (4) Date: Aug. 24, 2006

(87) PCT Pub. No.: WO2005/085293

PCT Pub. Date: Sep. 15, 2005

(65) Prior Publication Data

US 2007/0203094 A1    Aug. 30, 2007

(30) Foreign Application Priority Data

Feb. 26, 2004   (IT) .......................... MI2004A0347

(51) Int. Cl.
*C08B 37/08* (2006.01)
(52) U.S. Cl. ..................................... 536/55.3; 536/55.1
(58) Field of Classification Search .................. None
See application file for complete search history.

(56) References Cited

U.S. PATENT DOCUMENTS 4,788,187 A * 11/1988 Kuhla et al. ............. 514/211.01
5,612,321 A *  3/1997 Nguyen .......................  514/54
5,834,274 A * 11/1998 Hubbell et al. .............. 435/177

FOREIGN PATENT DOCUMENTS

EP       1082963        *  3/2001
WO   WO 2004/056877    *  7/2004

OTHER PUBLICATIONS

Smith, G. et al "Diacerhein treatment reduces the severity of osteoarthritis . . . " Arthritis Rheum. (1999) vol. 42, No. 3, pp. 545-554.*
Moreland, L. "Intra-articular hyaluronan (hyaluronic acid) and hylans for the treatment of osteoarthritis . . . " Arthritis Res. Ther. (2002) vol. 5, pp. 54-67.*
"Effect of Diacetyl Rhein on the Development of Experimental Osteoarthritis a Biochemical Investigation" by S.L. Carney; Dec. 1996; Osteoarthritis and Cartilage;Bailliere Tindall, London, GB; pp. 251-261; XP001056066; ISSN: 1063-4584; abstract.
"Hyaluronic Acid Hydrogel in the Treatment of Osteoarthritis" by R. Barbucci et al.; Dec. 2002; Biomaterials; Elsevier Science Publishers BV., Barking, GB; pp. 4503-4513; XP004377521; ISSN: 0142-9612; abstract.

* cited by examiner

*Primary Examiner*—Leigh C Maier
(74) *Attorney, Agent, or Firm*—Clifford W. Browning; Krieg DeVault LLP

(57) ABSTRACT

The present invention relates to esters of hyaluronic acid with rhein, more particularly to a compound based on hyaluronic acid, wherein alcohol groups of hyaluronic acid are esterified with rhein, to a process for preparing said ester and to a pharmaceutical composition comprising said ester.

14 Claims, 7 Drawing Sheets

# ESTERS OF HYALURONIC ACID WITH RHEIN, PROCESS FOR THEIR PREPARATION AND COMPOSITIONS COMPRISING THE SAME

This application claims the benefit of co-pending PCT Patent Application Serial No. PCT/IB2005/000506, filed Feb. 25, 2005, which is now International Publication Number WO 2005/085293, published Sep. 15, 2005, which claims priority to Italian Patent Application No. MI2004A000347, filed Feb. 26, 2004.

FIELD OF THE INVENTION

The present invention relates to esters of hyaluronic acid (HA) with rhein, more particularly to a compound based on hyaluronic acid, wherein alcohol groups of hyaluronic acid are esterified with rhein, to a process for preparing said compound and to a pharmaceutical composition comprising said compound.

PRIOR ART

Rhein is an alkaloid derived from senna which has anti-inflammatory and tissue-protecting properties.

Rhein, of which the chemical name is 4,5-dihydroxy-9,10-dihydro-9,10-dioxo-2-anthracene carboxylic acid, have the following general formula (I)

wherein R is H.

This substance is administered via the oral route, usually as diacetylrhein, a derivative of the above general formula (I) wherein each of the R groups is an acetyl group, which has greater bioavailability and which is used mainly in treating inflammation of the joints.

However, both rhein and diacetylrhein present the drawback of having a considerable laxative action, which can even lead to diarrhea and thus makes use thereof unadvisable for old or debilitated patients.

Moreover, on account of the insolubility of rhein and diacetylrhein in water, this side effect cannot be obviated by administering these active principles via the parenteral or intraarticular route.

Hyaluronic acid is a natural mucopolysaccharide formed of alternating units of D-glucuronic acid and N-acetylglucosamine, as represented in a general manner below Glucuronic acid    N-acetyl-glucosamine to form a linear chain having a molecular weight up to $13 \times 10^6$ Daltons.

Hyaluronic acid is present in all the soft tissues of the organism and in many physiological fluids such as, for example, the synovial fluid of the joints and the vitreous humor of the eyes.

Hyaluronic acid is used in many clinical applications under its acidic or salt form.

In particular, it is used with great success in inflammation of the joints, where it is administered by infiltration directly into the joint and acts by means of a dual mechanism: on the one hand by reducing the joint inflammation and on the other hand by increasing the viscosity of the synovial fluid, thereby benefiting the cartilage, which is more lubricated as a result.

It is also applicable in opthamology, where it is used for its protective and anti-inflammatory properties and for tissue repair, by virtue of its anabolic-reconstructive action on cartilage and skin.

However, hyaluronic acid is known to suffer from degradation.

It has been reported that the degradation of hyaluronic acid is caused by hydrolysis, depending on pH conditions and cation concentration [cf. e.g. Uchiyama H. et al. J. Biol. Chem. 1990; 265: 7753-7759; Tokita Y. and Okamoto A., Polymer Degr. and Stab. 1995; 48: 269-273; Hawkins C. L. and Davies M. J. Free Rad. Biol. Med. 1998; 24: 1396-1410; Schiller J. et al. Current Med. Chem. 2003; 10: 2123-2145].

After extensive studies, the present inventors have found that hyaluronic acid having alcohol groups esterified with rhein has surprisingly a higher stability than hyaluronic acid and further has an improved pharmacological activity compared to what is observed in respect of hyaluronic acid and rhein used separately.

Moreover, the present inventors have found that hyaluronic acid having alcohol groups esterified with rhein can be advantageously used by local administration, thereby avoiding the drawbacks associated with the oral administration of rhein.

The present invention has been achieved on the basis of these results.

SUMMARY OF THE INVENTION

According to a first aspect, the present invention relates to a compound based on hyaluronic acid, wherein alcohol groups of hyaluronic acid are esterified with rhein, as such or in derived form, or a salt thereof, which has not only a stability higher than the one of hyaluronic acid, but also an improved pharmacological activity compared to what is observed in respect of hyaluronic acid and rhein used separately, and further which can be used by local administration, thereby avoiding the drawbacks associated with the oral administration of rhein.

According to a second aspect, the present invention relates to a process for preparing the compound or a salt thereof according to the first aspect, which comprises reacting acid chloride of rhein, as such or in derived form, with hyaluronic acid.

According to a third aspect, the present invention relates to a pharmaceutical composition comprising the compound or a salt thereof according the first aspect in combination with suitable excipients and/or diluents.

According to another aspects, the present invention relates to a medicinal product or a medical device for human or veterinary use, formed by a composition according the third aspect, and to the use of a compound or a salt thereof according to the first aspect for preparing a medicament for treating inflammatory diseases, or for tissue repair, or for preparing biomaterials.

Other advantages of the present invention will appear in the following detailed description.

DETAILED DESCRIPTION OF THE INVENTION

Figure 1:
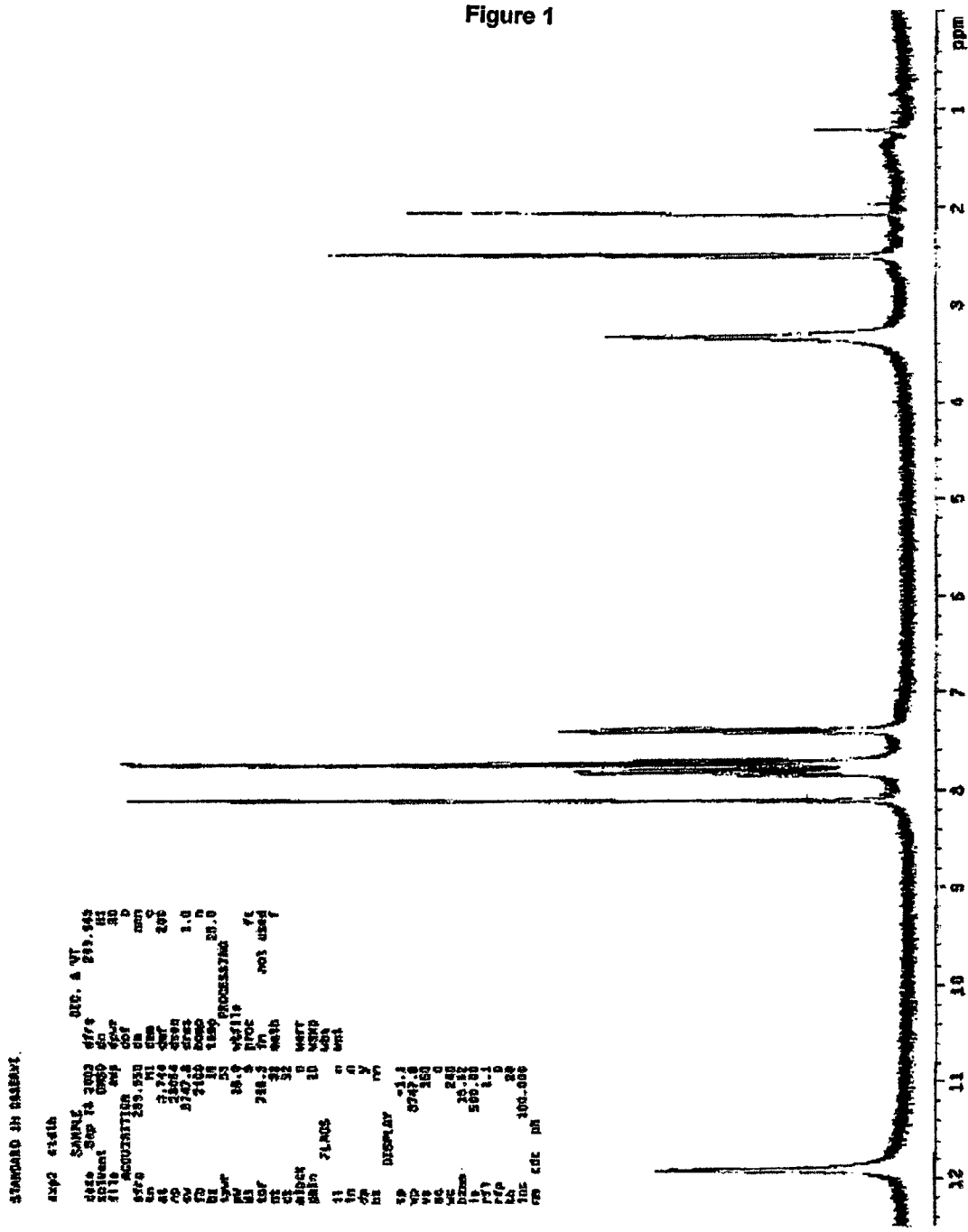
FIG. 1 shows the $^1$H-NMR spectrum of rhein obtained by saponication of the HA-Re compound of the present invention.

The present invention will be now described in a more detailed manner.

The present invention provides a compound based on hyaluronic acid, wherein alcohol groups of hyaluronic acid are esterified with rhein, as such or in derived form, or a salt thereof.

In the present description, the compound of the present invention will be also designated as "HA-Re compound".

It is to be noted that in the present description and claims, the term "rhein" means rhein as such or in derived form.

Salts of the HA-Re compound according to the present invention include preferably pharmaceutically acceptable salts, for example a sodium salt, a potassium salt, a magnesium salt, a calcium salt, or other conventional pharmaceutically acceptable salts, more preferably the sodium salt.

According to the present invention, the term "derived form" of rhein includes any derivative of rhein which is pharmacologically active in vivo and in which the acid group of rhein is available to form the ester bond with the hydroxyl groups of hyaluronic acid.

Preference is given to derivatives of rhein which make said anthraquinone available in vivo.

Examples of rhein in derived form according to the present invention include rhein as represented by the following formula

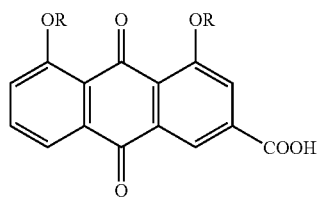

wherein R is independently any appropriate hydroxy-protecting group, preferably an acyl group, for example an acetyl, propionyl, butyryl or pivaloyl group, without being limited to these.

In a preferred embodiment of the present invention rhein is in derived form, and more preferably is diacetylrhein.

According to the present invention, rhein preferably esterifies at least 5% of the esterifiable alcohol groups of hyaluronic acid, more preferably between 5 and 50%, and even more preferably between 5 and 20%.

Particular preference is given to a compound wherein rhein esterifies 10% of the esterifiable alcohol groups of hyaluronic acid.

Said HA-Re compound may be prepared by a process according to the invention, which comprises reacting acid chloride of rhein with hyaluronic acid, preferably in an amount such that a percentage ratio between the mmol of acid chloride of rhein and the meq. of the esterifiable alcohol units of hyaluronic acid is greater than 5%, more preferably between 5% and 50%, even more preferably between 5% and 20%, and according to one particularly preferred embodiment 10%.

The selected process took due account of the choice of solvents depending on the acceptability of their residues (ICH—International Conference of Harmonisation of Technical Requirements for Registration of Pharmaceuticals for Human Use).

Preferably, the above-mentioned process according to the present invention comprises the following steps:
  a) preparing a suspension of hyaluronic acid in an aprotic non-polar solvent,
  b) adding acid chloride of rhein dissolved in a minimum amount of an aprotic non-polar solvent and a hydrogen ion acceptor,
  c) leaving the mixture to stir at reflux for a time that is sufficient for the esterification reaction to take place, and
  d) evaporating off the solvent.

Examples of aprotic non-polar solvents which may be used in step a) include cyclohexane, tetrahydrofuran, toluene, dichloromethane, n-hexane, more preferably cyclohexane.

Aprotic non-polar solvent which may be used to dissolve acid chloride of rhein is not limited, but should be preferably selected to be the same as the one used in step a).

Examples of the hydrogen ion acceptor which may be added in step b) include pyridine, triethylamine, more preferably Et$_3$N;

The time during which the reaction is left at reflux is not limited, but should be preferably for at least 20 hours.

Hyaluronic acid which may be used for preparing the HA-Re compound according to the present invention has preferably a molecular weight from 500,000 to 3,000,000 Da, more preferably around 600,000 Da.

The molecular weight of hyaluronic acid may be determined according to a conventional manner, for example by gel permeation chromatography (GPC).

Hyaluronic acid which is used for preparing the HA-Re compound according to the present invention may be commercially available (for example from Fidia Farmaceutici SpA—Abano T. PD) or can be prepared for example through extraction from rooster combs, through fermentation of bacteria bearing a mucin layer or through other conventional manners [cf. Proteoglycan Protocols, Humana Press, R. V. Iozzo Ed. Totowa, 2001].

The acid chloride of rhein which may be used in the process for preparing the HA-Re compound according to the present invention may be obtained by means of a process comprising the following steps:
  a') preparing a suspension of rhein in an aprotic non-polar solvent;
  b') adding an amount of SOCl$_2$ so as to obtain a molar ratio between SOCl$_2$ and rhein of greater than 10;

c') leaving the reaction to stir at reflux in an inert atmosphere for a time that is sufficient for the rhein acid chloride to form; and d') removing the solvent and the excess of unreacted $SOCl_2$ by distillation.

Examples of aprotic non-polar solvents which may be used in step a') include cyclohexane, tetrahydrofuran, toluene, dichloromethane, n-hexane, preferably a chloride solvent and more preferably $CH_2Cl_2$.

The time during which the reaction is left at reflux in step c') is not limited, it should be preferably for at least 3 hours Rhein, as such or in derived form, which may be used in step a') for preparing the acid chloride of rhein may be commercially available (for example from Aldrich) or may be synthesized according to conventional processes [cf. Nawa H et al. J. Org. Chem. 1961; 26: 979-981 and references herein reported; Smith C. W. et al. Tetrahedron Lett. 1993; 34: 7447-7450; Gallagher P. T. et al. Tetrahedron Lett. 1994; 35: 289-292].

According to one particularly preferred application, the HA-Re compound of the present invention obtained using the process according to the present invention is purified.

This purification is preferably carried out using a dialysis membrane.

In this case, as will be described in the examples which follow, preference is given to using the dialysis membrane which is commercially available under the trade name "Slide-A-Lyzer 3.5K" (Pierce, Rockford, Ill. USA), following the manufacturer's instructions.

As already discussed above, HA-Re compound of the present invention has an advantageous high stability, being stable for at least 36 months at a temperature of 4° C.±0.5° C. in aqueous solution, preferably buffered at pH 7.4, such as for example a phosphate-buffered saline solution prepared according to the Official Italian Pharmacopoeia, XI edition.

The HA-Re compound according to the present invention has anti-inflammatory, healing, reconstructive and anabolic properties for the skin and cartilage.

The present invention therefore also relates to a pharmaceutical composition comprising a HA-Re compound according to the present invention in combination with suitable excipients and/or diluents.

In particular, the pharmaceutical composition according to the present invention may be a medical device and/or a medicinal product for human and veterinary use.

The pharmaceutical composition according to the present invention preferably has a formulation suitable for loco-regional administration.

A particularly preferred pharmaceutical composition according to the present invention is a composition suitable for use via intraarticular infiltration, via ophthalmic administration, for example eye drops and ophthalmic ointments, and via topical administration.

Preferably, the composition of the invention is in the form of an aqueous dispersion.

Said dispersion is preferably in a buffer solution having a physiological pH, more preferably a pH of 7.4, for example a phosphate-buffered saline solution prepared according to the Official Italian Pharmacopoeia, XI edition.

According to one particularly preferred application, in the pharmaceutical composition of the present invention, the HA-Re compound or a salt thereof according to the present invention is present in a concentration ranging from 0.5% to 2% w/v, preferably in a concentration of 1% w/v.

Another object of the present invention is the use of the HA-Re compound or a salt thereof according to the present invention for preparing a medicament for treating inflammatory diseases, preferably including inflammatory diseases of the joints, in particular osteoarthritis and rheumatoid arthritis.

A further object of the present invention is also the use of the HA-Re compound or a salt thereof according to the present invention for preparing a medicament for tissue repair, in which said tissue is cartilage or skin.

Moreover, the HA-Re compound or a salt thereof according to the present invention can be used to prepare biomaterials, for example gauzes for treating wounds or burns and matrices for cell growth to be used in the treatment of burns and in implantology.

The present invention will be better illustrated by the following experimental Examples as well as Figures.

EXAMPLES

Example 1

Preparation of Acid Chloride of Rhein

Rhein (provided by Aldrich) (21.5 mg; 0.075 mmol) was placed in a 50 ml round-bottomed flask and $CH_2Cl_2$ (15 ml) was added thereto. The suspension turned an orange colour. Then, $SOCl_2$ (0.5 ml; 6.9 mmol) was added to the suspension. The reaction was carried out with stirring at reflux (50° C.) in an inert atmosphere ($N_2$). The reaction mixture was left at reflux for 3 hours and the solution turned a clear orange-yellow colour. In order to remove the $CH_2Cl_2$ and the excess of unreacted $SOCl_2$, toluene (approximately 5 ml) was added and the mixture was distilled at 500 mmHg, corresponding to $6.6 \times 10^4$ Pa, at least 4 times to obtain 23 mg of crude acid chloride of rhein (yield:quantitative). The product was identified by TLC, ethyl acetate.

Example 2

Preparation of the HA-Re Compound

Hyaluronic acid (provided by Fidia Farmaceutici SpA-Abano T. PD; average molecular weight of approximately 600,000 Da) (277.3 mg; $4.6 \times 10^{-4}$ mmol;

corresponding to 0.75 meq. of esterifiable primary alcohol units) was suspended in cyclohexane (20 ml). Acid chloride of rhein prepared as described in Example 1 (21.5 mg; 0.075 mmol) dissolved in a minimum amount of $CH_2Cl_2$ was added. Then, $Et_3N$ (3 ml) was added. The suspension turned a red colour. The reaction was carried out with stirring at reflux (70° C.) in an inert atmosphere ($N_2$). After a short time, the suspension turned a red-orange colour, which became darker after approximately three hours. After 20 hours, the reaction was stopped and the solvent was evaporated off under reduced pressure (650 mmHg, corresponding to $8.7 \times 10^4$ Pa) to dryness, resulting in the HA-Re compound in the form a clear yellow precipitate.

Example 3

Purification of the HA-Re Compound a) Preparation of the Sample

A phosphate-buffered saline solution (5 ml) at pH 7.4 was added to the HA-Re compound (0.1019 g) obtained as described in Example 2. A two-phase system was obtained and the solution turned an orange-yellow colour while the residue was represented by a mass of yellow-brown colour of gelatinous consistency. After a wait of at least 24 hours, a viscous colloidal system of brown colour was obtained.

b) Purification

A dialysis membrane "Slide-A-Lyzer® 3.5K" (Pierce, Rockford, Ill. USA) was left to hydrate in an appropriate manner with phosphate-buffered saline solution at pH 7.4. Following the manufacturer's instructions, a suitable amount of the HA-Re compound to be purified was introduced. Dialysis was carried out for 2 hours against a phosphate buffer at pH 7.4 (after only 20 minutes the buffer solution appeared to be slightly yellow in colour). The operation was repeated at least three times until the buffer solution remained colourless, testing for the absence of absorption in the visible spectrum. The purified HA-Re compound was recovered from the membrane by dialysis. The purity of HA-Re compound thus obtained was 99.8%.

Example 4

Analysis of the HA-Re Compound of the Present Invention Obtained

1) Test Using a UV-VIS Spectrophotometer

The concentration of rhein in the purified HA-Re compound obtained as described in Example 3 was evaluated by taking a spectrophotometric reading at 430 nm based on the "robust" calibration in the range $10^5$-$10^{-3}$ ($R^2$=0.9999). This wavelength was selected since hyaluronic acid absorbs in the UV range, which thus renders difficult the quantitative determination of rhein. Based on the spectrophotometric reading, the esterification reaction yield based on rhein was found to be 58%.

Considering Example 2, the quantity of rhein used in the reaction was selected to esterify a maximum of 10% of esterifiable primary alcohol groups of hyaluronic acid. Since the esterification reaction yield based on rhein was found to be 58%, it may be estimated that 5.8% of esterifiable alcohol groups of hyaluronic acid were esterified.

2) $^1$H-NMR Analysis

A $^1$H-NMR spectrum of the HA-Re compound obtained in Example 2 was carried out in deuterated buffer solution using a Varian VRX300 spectrometer. However, problems were encountered when interpreting this spectrum since the percentage of rhein which reacts with the hyaluronic acid did not make it possible to identify the aromatic ring. Taking account of the poor solubility of rhein in an aqueous environment and considering that esterification is a reversible reaction, saponification, i.e. basis hydrolysis, was therefore carried out so as to obtain the rhein from the HA-Re compound. The saponification compound obtained was precipitated. A $^1$H-NMR spectrum of the saponification compound thus obtained was carried out in dimethylsulphoxide (DMSO) using the Varian VRX300 spectrometer. The spectrum obtained, which is shown in FIG. 1, coincided completely with that of rhein.

3) I.R Analysis

Figure 2:
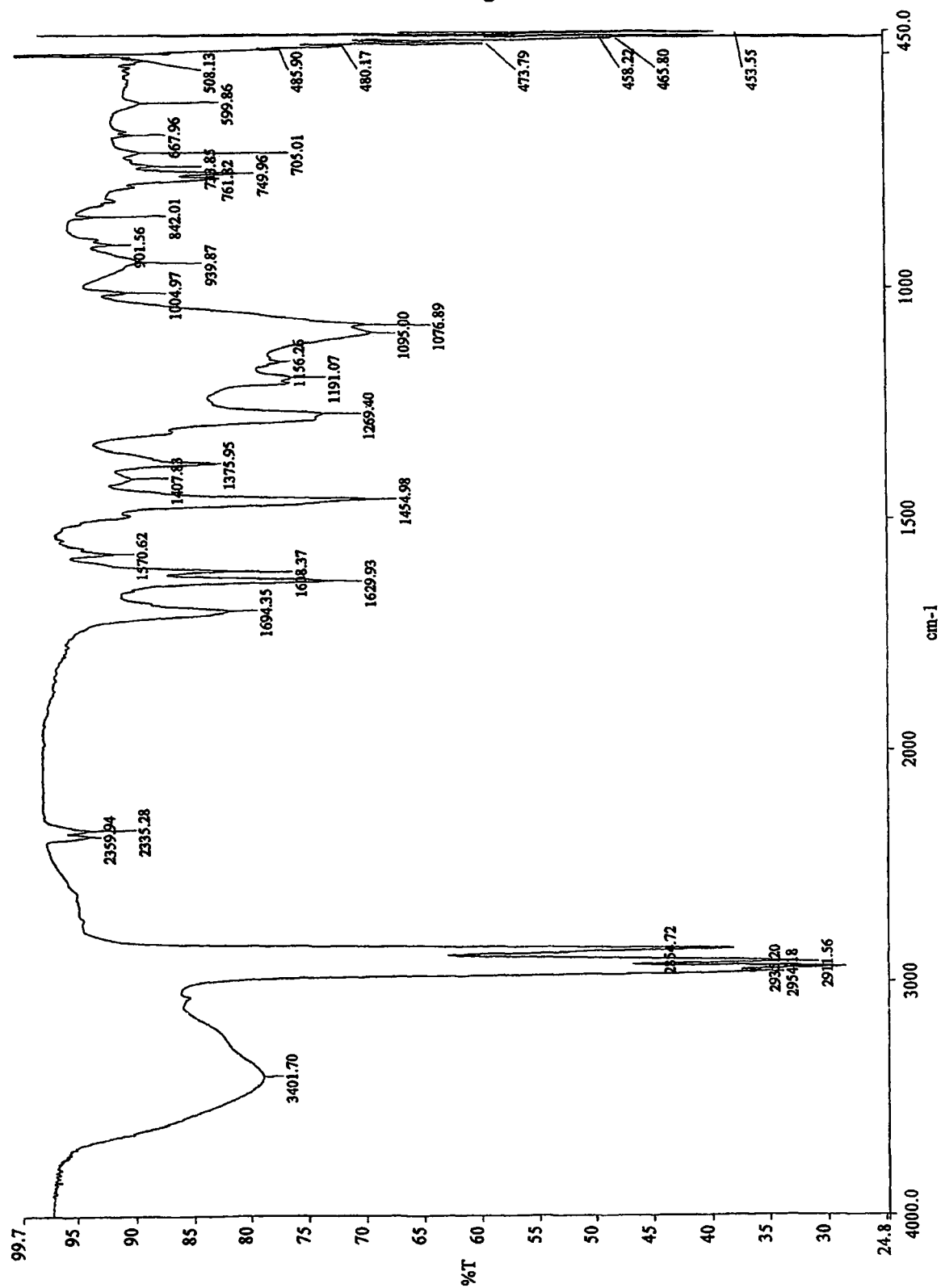
FIG. 2 shows the I.R. spectrum of rhein obtained by saponication of the HA-Re compound of the present invention.

An I.R. spectrum was carried out in Nujol for the compound obtained from the saponification of HA-Re compound of the present invention (using the Spectrum BX FT-IR System, Perkin Elmer). As shown in FIG. 2, the spectrum obtained coincides with that of pure rhein.

4) HPLC-MS

Figure 3:
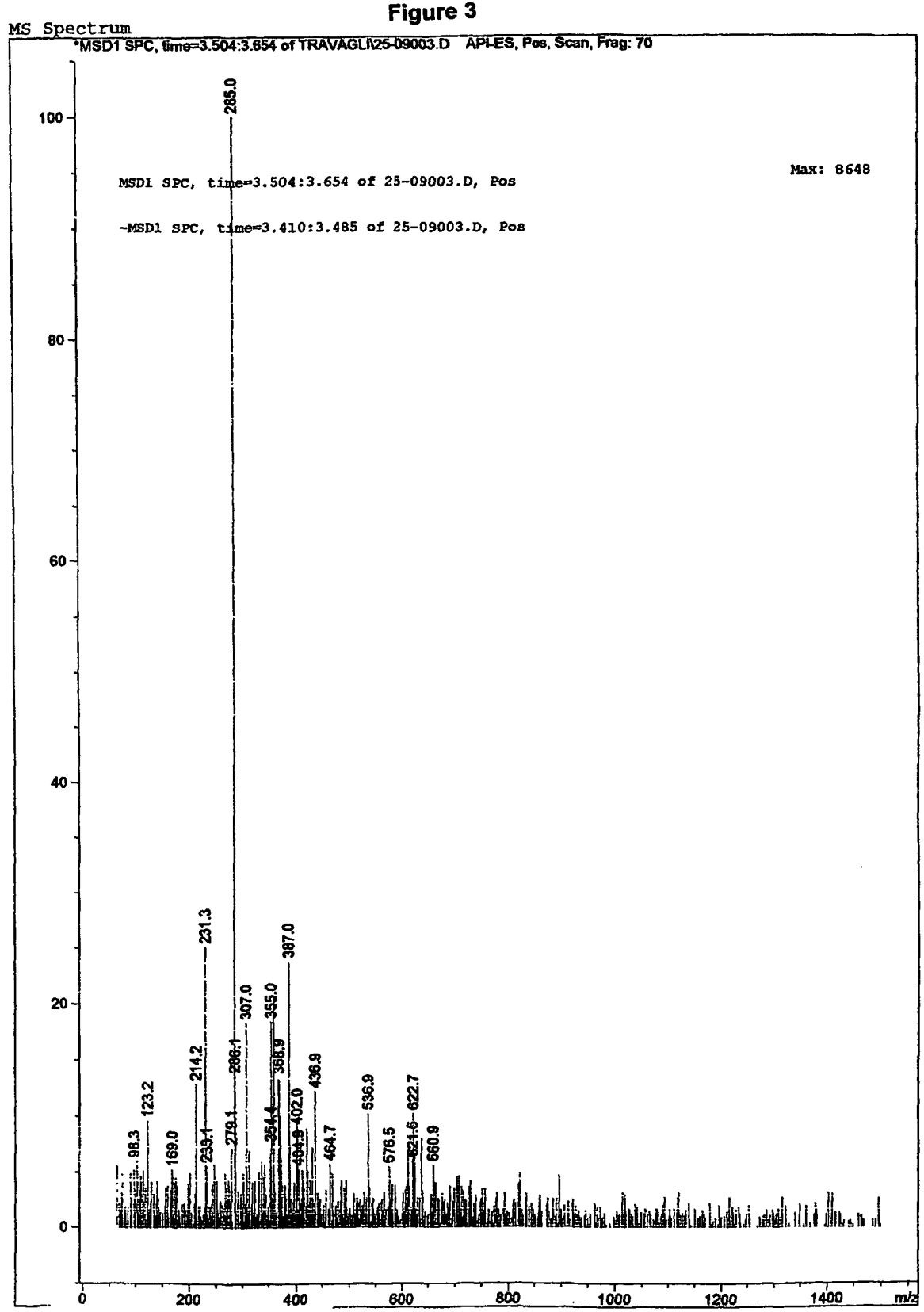
FIG. 3 shows the HPLC-MS analysis of rhein obtained by saponication of the HA-Re compound of the present invention, FIG. 4 reports the results obtained in RT-PCR experiments comparing the effect of hyaluronic acid at the pharmacological concentration to the effect of HA-Re compound of the invention at the same concentrations.

An HPLC-MS analysis was carried out (using the equipment Agilent 1100, series LC/MSD) on the compound obtained from the saponification of the obtained by saponication of the HA-Re compound of the present invention, using as the mobile phase a mixture of methanol/water 80:20 containing 2.5% formic acid, at a flow rate of 0.8 ml/min. As can be seen from FIG. 3, the mass of the compound corresponds to that of rhein.

Example 5

Evaluation of the Technological Characteristics of the HA-Re Compound of the Invention 1) Evaluation of the Hydrolytic Stability The HA-Re compound the invention as obtained in Example 2 and not purified by means of dialysis was stored for more than six months in the dry state in vials, in the dark and at ambient temperature (22° C.). This sample was then purified by means of dialysis as described in Example 3 and the concentration of rhein was evaluated using a UV-VIS spectrophotometer. The concentration was found to be equal to that obtained for the product synthesized immediately. The experimental results therefore show that, in the dry state, no degradation was observed. Moreover, the HA-Re compound of the invention produced as described in Example 2 and purified by means of dialysis as described in Example 3 was stored for six months in a 2% solution in phosphate buffer pH 7.4, in vials, in the dark and at a temperature of 4° C. The presence of foreign bodies was found in the sample, due to the use of non-sterile material and to the fact that no preservatives were used. The sample was once again subjected to dialysis using the same method as described in Example 3, with it being subjected to dialysis for at least four days. By means of a UV-VIS test, it was not possible to find any rhein released into the various buffer solutions used for the dialysis. In this case too, therefore, the compound was shown to be chemically stable since no release of rhein from the HA-Re compound was found, at least in terms demonstrable using current analytical techniques. Therefore, even in solution, no hydrolytic degradation was observed.

The results obtained make it possible to state that the HA-Re compound according to the invention is stable for at least 24 months under refrigerated conditions (at 4° C.±0.5° C.) in aqueous solution. This statement derives from the absence of any noticeable hydrolytic degradation.

Moreover, in order to rule out the possibility that hydrolytic degradation of the hyaluronic acid occurs during the esterification reaction with rhein, a blank test of said reaction was carried out. In particular, the same conditions were used as in the reaction of bonding rhein to hyaluronic acid, but in the absence of said rhein. In particular, hyaluronic acid (100 mg) was added into a mixture of cyclohexane (10 ml), dichloromethane (1 ml) and triethylamine (1 ml) and the reaction was carried out at reflux (70° C.) in an inert atmosphere ($N_2$) for 24 hours; once this time had elapsed, the reaction solvents were removed under a nitrogen atmosphere. The compound obtained was much less soluble in water than hyaluronic acid in the native state and was characterized by a non-determinable viscosity after 24 hours of dispersion. This means that depolymerization can be ruled out, as this would have resulted in water-solubility and therefore to a reduction in viscosity.

Finally, a check was made of the hydrolytic stability of the purified HA-Re compound of the invention as obtained in Example 3 upon sterilization. As discussed above, it was found that the use of non-sterile material and the fact that preservatives are not used leads to the presence of foreign bodies in the samples of the compound of the invention. In particular 1% solution of the HA-Re compound of the invention, purified using a dialysis membrane, in a phosphate-buffered saline solution at pH 7.4 was prepared. Given experimental evidence which showed hyaluronic acid to be a heat-sensitive molecule (Biomaterials 23 (2002) 4503-4513), the sample thus obtained was sterilized using pressurized saturated steam in an autoclave for 20 minutes at 121° C. The sample was then subjected to dialysis once again in a dialysis membrane in order to evaluate any presence of rhein in the dialysed liquid; no trace of rhein was found. These results allow the conclusion to be drawn that the sample is hydrolytically stable upon hot sterilization.

2) Analysis of the Rheological Characteristics and of the Syringeability

The syringeability of the HA-Re compound of the invention was analysed in comparison to that of hyaluronic acid both with a high and a low molecular weight.

In particular, the following three samples were prepared:
a) a 1% w/v solution of high molecular weight hyaluronic acid (average molecular weight approximately 1'200'000) in phosphate-buffered saline solution, pH 7.4
b) a 1% w/v solution of low molecular weight hyaluronic acid (average molecular weight approximately 600'000) in phosphate-buffered saline solution, pH 7.4
c) a 1% w/v solution of the HA-Re compound of the invention in phosphate-buffered saline solution, pH 7.4.

The viscosity of the samples was then measured using a VISCOMATE MODEL VM-10A (glass vial: 3 ml; in the absence of stirring conditions; temperature 20±0.2° C.), with the following values being obtained:
a) $\eta$=78.4 mPa·s
b) $\eta$=64.8 mPa·s
c) $\eta$=47.9 mPa·s The results obtained show that the HA-Re compound of the invention has better syringeability than hyaluronic acid in the native state both with a high and a low molecular weight. This is because a 1% w/v solution of the HA-Re compound of the invention has a lower viscosity than a 1% w/v solution of low molecular weight hyaluronic acid, which in turn has a lower viscosity than a 1% w/v solution of high molecular weight hyaluronic acid.

The reduction in viscosity which was observed, having demonstrated that there is no depolymerization reaction of the hyaluronic acid after the esterification reaction, can be attributed to the covalent interaction between rhein and hyaluronic acid.

Example 6

Evaluation of the Pharmacological Activity In Vitro of the HA-Re Compound of the Invention Normal cartilage biopsies were obtained from 5 individuals (3 male and 2 female, mean age: 59.3±5.1 years) during hip or femur surgery as a result of traumatic fracture. The subjects chosen for the study did not present biochemical or clinical sign of inflammatory or joint diseases, and presented normal cartilage at both macroscopic and microscopic levels. Cartilage was collected under sterile conditions and immediately processed for chondrocyte isolation. The samples were first cleaned of any adherent muscular, connective or subchondral bone tissues, then minced into 1-3 $mm^3$ fragments and rinsed in phosphate buffered saline, pH 7.2 (PBS). Single chondrocytes were then released by repeated enzymatic digestions of 60-75 min. at 37° C. with 0.25% trypsin, 400 U/ml collagenase I, 1000 U/ml collagenase II and 1 mg/ml hyaluronidase. The cells were pooled, washed extensively in PBS and seeded at high density in 35 mm plates (45×$10^3$ cells/$cm^2$). Culture medium was Coon's modified Ham's F12 supplemented with 10% FCS (Mascia Brunelli, Milano, Italy). Maintenance of the chondrocyte phenotype was estimated by the detection of type II collagen after pepsin digestion of the culture supernatant. Cell viability was evaluated by the Trypan-Blue exclusion test. Cell duplication was determined at regular intervals by trypsinization of the culture and cell number quantification. The experiments of stimulation were performed when the primary cultures reached confluence (passage 0). The cells were then cultured for 2 days in the presence of ascorbic acid (50 μg/ml) and incubated thereafter for 20 h in the absence or presence of (rh)IL-1$\beta$ (5 ng/ml), with or without the addition of various concentrations of hyaluronic acid (HA), compound of the invention (HA-Re) or rhein.

Both hyaluronic acid and rhein have been reported to have beneficial effects in osteoarthritis due to their ability to inhibit the activity of metalloproteinases (MMP) involved in cartilage catabolism.

In order to study the effect of various compounds on MMP expression in human chondrocytes we performed Real Time-PCR assays. Total RNA was extracted from the cultured human chondrocytes using Trizol (Gibco BRL) according to the manufacturer's instructions. Strands of cDNA were synthesized using a Superscript First-Strand synthesis kit (Gibco BRL) with 1 μg total RNA. The primers were as follows:

```
MMP-1 (collagenase)
Sense:              5'-CTGAAGGTGATGAAGCAGCC-3'
Antisense:          5'-AGTCCAAGAGAATGGCCGAG-3;
(fragment size 428
bp)

MMP-3 (stromelysin)
Sense:              5'-CCTCTGATGGCCCAGAATTGA-3',
Antisense:          5'-GAAATTGGCCACTCCCTGGGT-3';
((fragment size 440
bp)

Glyceraldehyde-3-
phosphate
dehydrogenase
(GAPDH),
Sense:              5'-CCACCCATGGCAAATTCCATGGCA-3';
Antisense:          5'-TCTAGACGGCAGGTCAGGTCCA.
(fragment size 598
bp)
```

Amplification was performed at 60-64° C. for 45 cycles in iCycler Thermal Cycler (Bio-Rad Hercules, Calif.), and data were analyzed using iCycler iQ Optical System Software. The relative expression in each sample was calculated by a mathematical method based on the real-time PCR efficiencies using as references GAPDH mRNA. All samples were assayed in triplicate. After 45 amplification cycles, threshold cycle values were automatically calculated, and femtograms of starting cDNA were calculated from a standard curve covering a range of four orders of magnitude. Both MMPs and GAPDH standard curves ranged from 1 to 1000 femtograms per 25-μl reaction. Ratios of MMPs to GAPDH starting quantity were calculated. Statistical differences of results between various experimental variables and relevant controls were analyzed using the Student t test.

Figure 4:
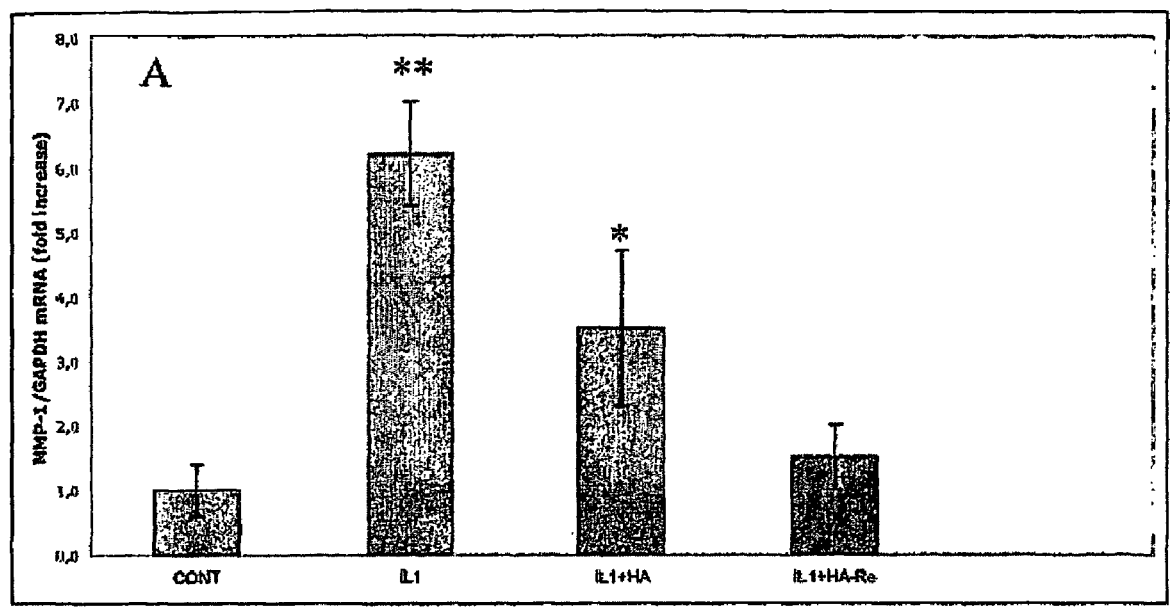
Figure 4:
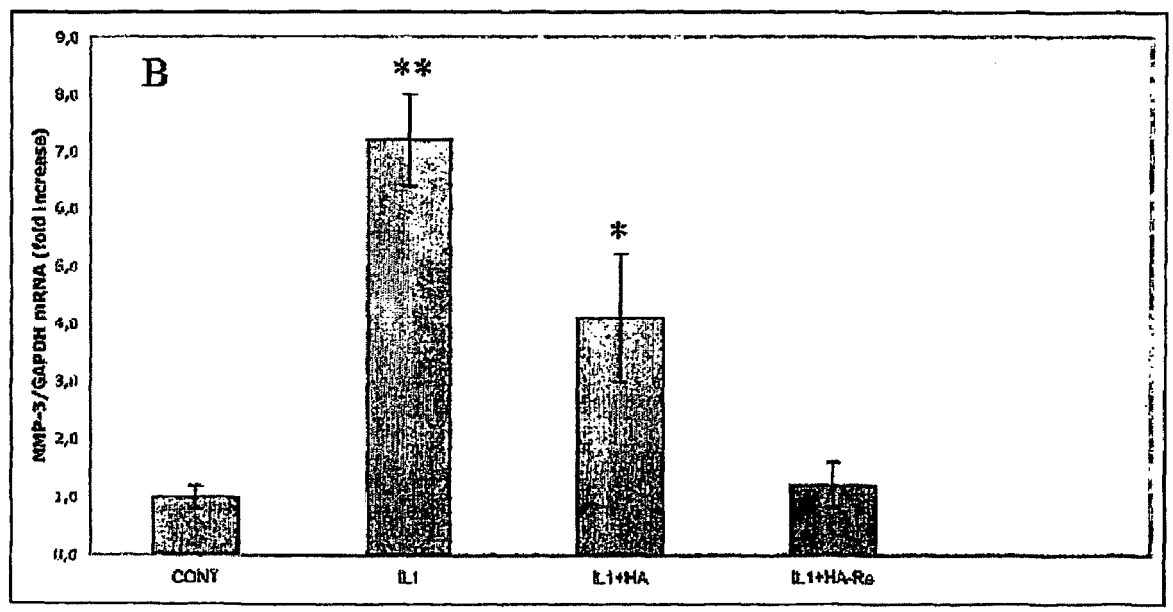
Figure 5:
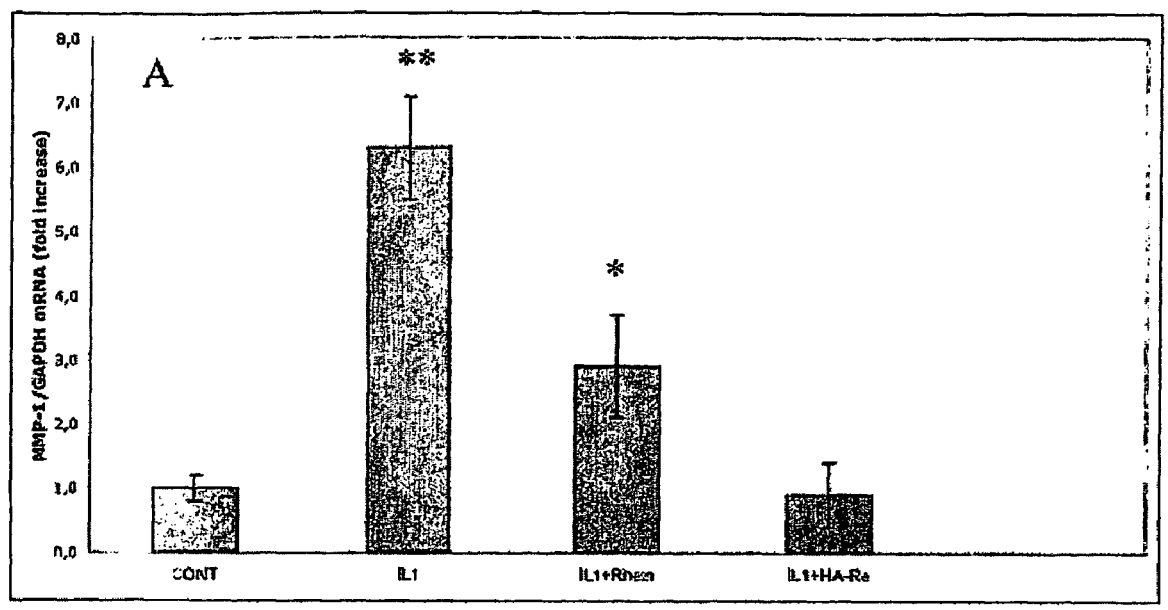
FIG. 5 reports the results of RT-PCR experiments in which the effect of rhein at pharmacological dose has been compared to the effect of a similar dose of HA-Re compound of the present invention.
Figure 5:
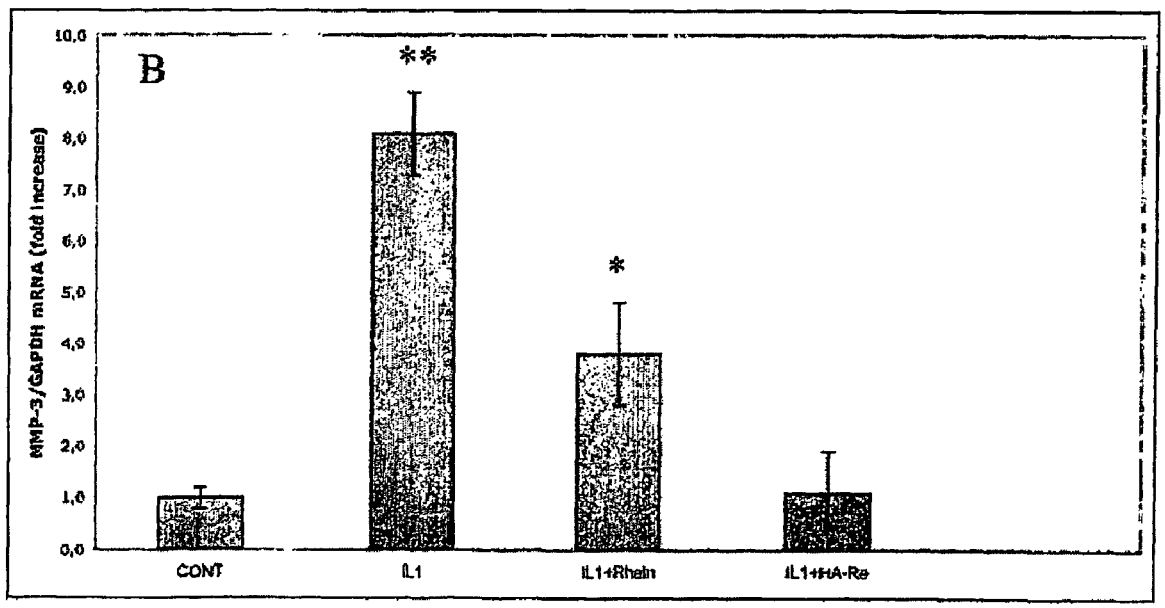

FIGS. 4 and 5 report the results obtained in RT-PCR experiments.

All samples were assayed in triplicate. In each experiment, the change of MMPs mRNA expression was expressed as fold-increase as compared to that of untreated cells. Mean and standard deviation of three experiments are shown. Paired student's t test was used to determine the significance of the effects of various treatments. Statistical difference between treatment and control groups are also reported:

*=p<0.01; **=p<0.001 (Student t test).

IL-1 treatment led to a dramatic increase in the expression of both MMP-1 and MMP-3, consistent with literature data. In the experiments reported in FIG. 4 we have compared the effect of HA at the pharmacological concentration commonly reported in the literature (1 mg/ml) to the effect of HA-Re (compound of the invention) at the same concentrations (1 mg/ml). Similar results were obtained in a range of 0.1-1.5 HA concentrations. Exposure of human chondrocytes to HA at pharmacological dose (1 mg/ml) was able to significantly prevent MMP1 and MMP2 induction by IL1 (FIGS. 4 A and B). Surprisingly, similar doses of HA-Re compound of the invention led to an even more dramatic protective effect, with MMP expression brought back to basal level in spite of IL1 exposure. FIG. 5 reports the results of experiments in which the effect of rhein at pharmacological dose (10 μM) has been compared to the effect of a similar dose of HA-Re. It also appears that HA-Re compound of the invention) is more potent than Re alone in achieving a down regulation of IL1-induced MMP expression.

Example 7

An additional synthesis of HA-Re according to the present invention was performed as in Example 2, except that 20 mg of hyaluronic acid and 23 mg of acid chloride of rhein were used, corresponding to stoichiometric concentrations of rhein and hyaluronic acid based on primary alcoholic groups of hyaluronic acid.

Figure 6:
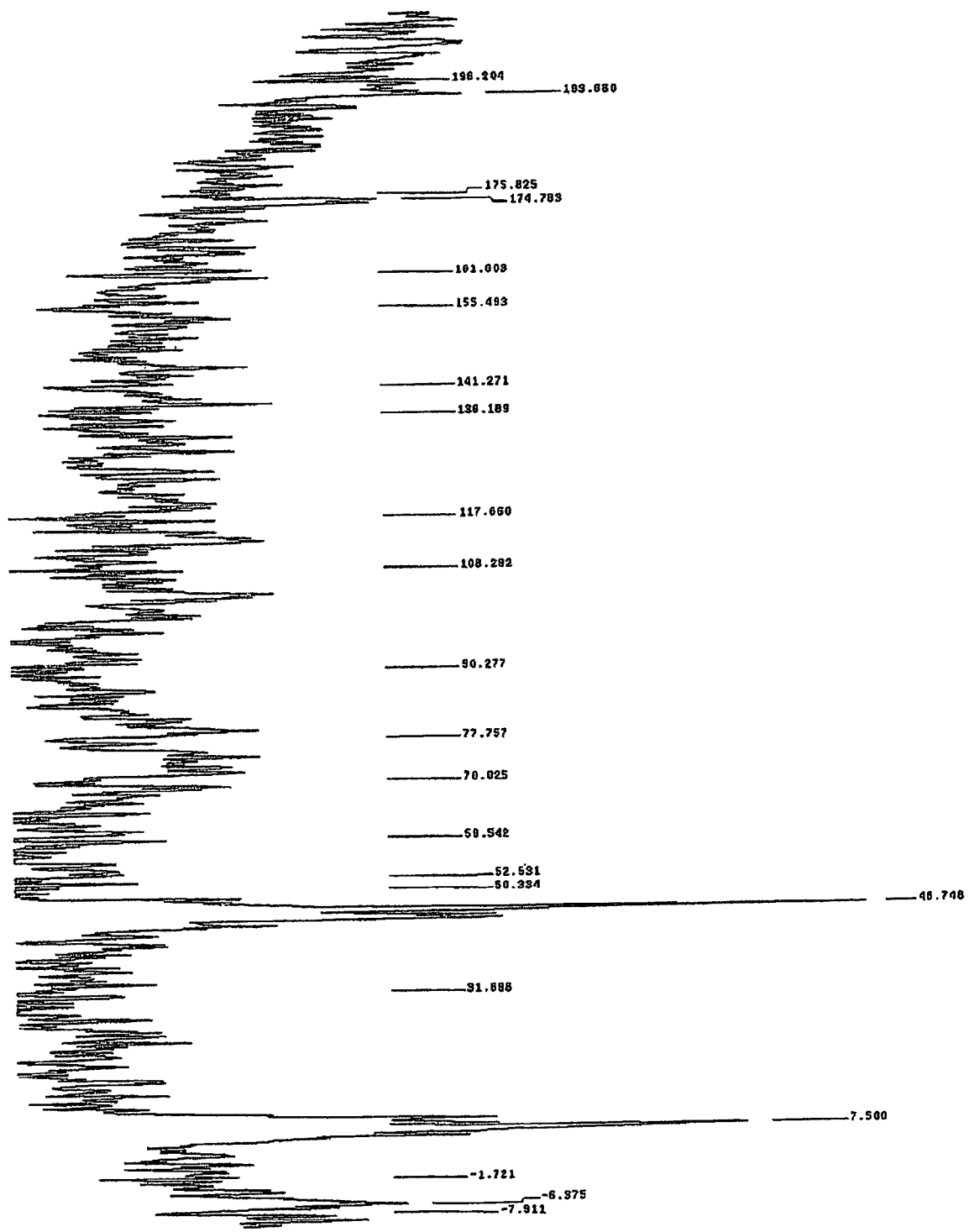
FIG. 6 shows the $^{13}$C-NMR spectrum of a HA-Re compound according to the present invention.

FIG. 6 shows the $^{13}$C-NMR spectrum of the thus obtained HA-Re compound according to the present invention, wherein a characteristic peek at 175 ppm, specific for ester functions, appears clearly.

Figure 7:
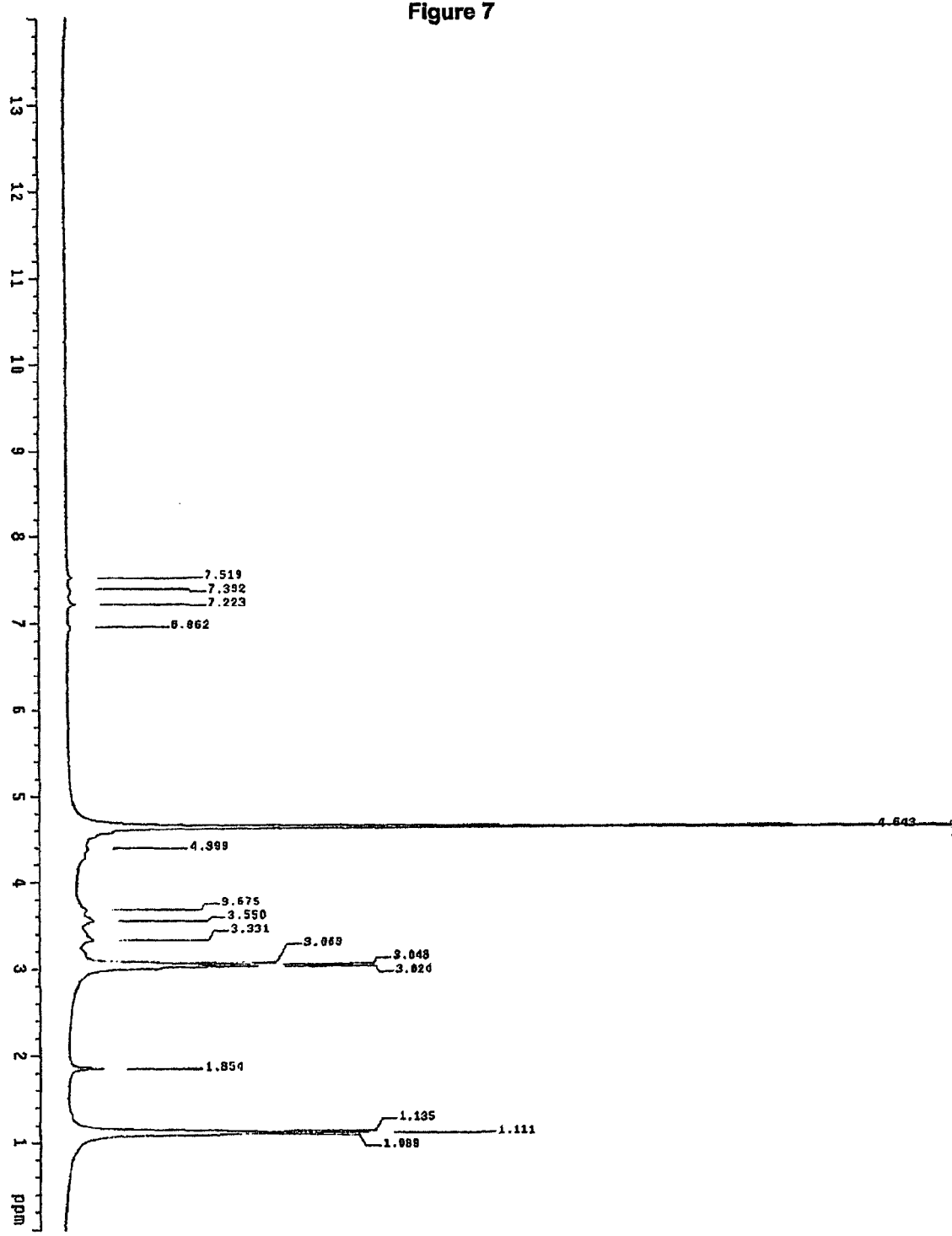
FIG. 7 shows the $^1$H-NMR spectrum of a HA-Re compound according to the present invention.

FIG. 7 shows the $^1$H-NMR spectrum of the thus obtained HA-Re compound of the present invention, wherein characteristic peeks between 7 and 8 ppm, specific for aromatic rings of rhein, appear clearly.

Therefore, it appears clearly from these two NMR spectra that in the HA-Re compound according to the present invention, rhein esterifies alcohol groups of hyaluronic acid.

The invention claimed is:

1. A process for preparing a compound based on hyaluronic acid, wherein alcohol groups of hyaluronic acid are esterified with rhein, as such or in derived form, or a salt thereof, which comprises the following steps:

a) preparing a suspension of hyaluronic acid in an aprotic non-polar solvent;
   b) adding acid chloride of rhein, as such or in a derived form, dissolved in an aprotic non-polar solvent and a hydrogen ion acceptor;
   c) leaving the mixture to stir at reflux for a time that is sufficient for the esterification reaction to take place; and
   d) evaporating off the solvent.

2. The process according to claim 1, wherein said aprotic non-polar solvent of step a) is cyclohexane.

3. The process according to claim 1, wherein in step b), said hydrogen ion acceptor is $NEt_3$.

4. The process according to claim 1, wherein in step c), the reaction is left at reflux for at least 20 hours.

5. The process according to claim 1, in which the acid chloride of rhein is obtained by means of a process comprising the following steps:

a') preparing a suspension of rhein in an aprotic non-polar solvent;
   b') adding an amount of $SOCl_2$ so as to obtain a molar ratio between $SOCl_2$ and rhein of greater than 10;
   c') leaving the reaction to stir at reflux in an inert atmosphere for a time that is sufficient for the rhein acid chloride to form; and
   d') removing the solvent and the excess of unreacted $SOCl_2$ by distillation.

6. The process according to claim 5, wherein said aprotic non-polar solvent of step a') is a chloride solvent.

7. The process according to claim 6, wherein said chloride solvent is $CH_2Cl_2$.

8. The process according to claim 5, wherein in step c'), the reaction is left at reflux for at least 3 hours.

9. The process according to claim 1, which further comprises a final step of purification.

10. The process according to claim 9, wherein said purification step is carried out using a dialysis membrane.

11. The process according to claim 1, wherein the acid chloride of rhein and the hyaluronic acid are in an amount such that a percentage ratio between the mmol of acid chloride of rhein and the meq. of the esterifiable alcohol units of hyaluronic acid is at least 5%.

12. The process according to claim 11, wherein said percentage ratio ranges from 5% to 50%.

13. The process according to claim 12, wherein said percentage ratio ranges from 5 to 20%.

14. The process according to claim 13, wherein said percentage ratio is 10%.

* * * * *